United States Patent [19]

Kamstra

[11] Patent Number: 4,573,972
[45] Date of Patent: Mar. 4, 1986

[54] AUTOMATIC INJECTION DEVICE

[75] Inventor: Paulus R. Kamstra, Olst, Netherlands

[73] Assignee: Duphar International Research B.V., Weesp, Netherlands

[21] Appl. No.: 560,935

[22] Filed: Dec. 13, 1983

Related U.S. Application Data

[63] Continuation-in-part of Ser. No. 405,367, Aug. 5, 1982, Pat. No. 4,529,403.

[30] Foreign Application Priority Data

Aug. 10, 1981 [NL] Netherlands ................... 8103744

[51] Int. Cl.$^4$ .............................................. A61M 5/08
[52] U.S. Cl. .................................................... 604/191
[58] Field of Search ............... 604/238, 232, 191, 134, 604/135, 235, 203, 89–91

[56] References Cited

U.S. PATENT DOCUMENTS

| | | | |
|---|---|---|---|
| 3,330,282 | 7/1967 | Visser et al. | 604/90 |
| 4,235,235 | 11/1980 | Bekkering | 604/238 |
| 4,394,863 | 7/1983 | Bartner | 604/191 |
| 4,413,991 | 11/1983 | Schmitz et al. | 604/191 |
| 4,469,482 | 9/1984 | Lissenburg et al. | 604/238 |

Primary Examiner—C. Fred Rosenbaum
Assistant Examiner—Christa K. Scott
Attorney, Agent, or Firm—Stevens, Davis, Miller & Mosher

[57] ABSTRACT

An automatic device for injecting two or more different injection liquids which may not be in contact with each other for long periods of time: a combination of a discharge mechanism, a cartridge holder and a cartridge which is slidably accommodated in the holder and which includes an ampoule, a piston which is movable in the ampoule and seals same, and a hypodermic needle connected to the front of the ampoule by means of a needle mount.

10 Claims, 3 Drawing Figures

AUTOMATIC INJECTION DEVICE

This application is a continuation-in-part of copending application Ser. No. 405,367, filed Aug. 5, 1982 now U.S. Pat. No. 4,529,403.

The invention relates to an automatic device for injecting two or more different injection liquids which may not be in contact with each other for longer periods of time, a so-called "plural injection device."

In an automatic injector, an ampoule and a hypodermic needle in operative association therewith is driven by the force of a power source so as to insert the needle and then to inject the injection liquid present in the ampoule. Such an injector comprises a combination of a discharge mechanism, a cartridge holder and a cartridge which is slidably accommodated in the cartridge holder and which comprises an ampoule, a piston which is movable in the ampoule and seals same, and a hypodermic needle which is connected to the front of the ampoule and, if desired, is covered by a flexible sheath to maintain the needle in a sterile condition. The discharge mechanism is provided with a power source which can move the cartridge from an inoperative condition to an operative condition. The injector furthermore comprises locking means to control the actuation of the power source and preferably a safety device to block said locking means.

Automatic injectors have been developed especially for use by persons who have to administer an injection into their own body at an instant which is not known beforehand. These persons include, for example, persons having an increased risk of a cardial infarct or soldiers after having been exposed to an enemy's battle gas, for example, a nerve gas. It will therefore be obvious that high requirements have to be imposed upon automatic injectors as regards the reliability and the handlability. Such injectors are usually stored for years at a stretch and in addition are carried with the potential user under varying conditions for a long period of time; the operation of the injector must be sufficiently ensured at the critical instant. When said critical moment has come, it must be possible to handle the injector rapidly and easily and to be used efficaciously.

It may be desired, however, to be able to inject several medicaments at that instant which are not compatible during the storage time. In particular for military applications, the administration of several medicaments or antidotes is often necessary, for instance to reach an effective therapy, or because it is not known beforehand which battle gas as to nature and composition will be used by the enemy. Said medicaments are often not compatible with each other during the long storage time of the injector.

It is not advisable to use several automatic injectors filled with different injection liquids in the above-described emergency situation: There is a fair chance that a mistake is made in choosing the correct injectors, it would last too long before all the desired medicaments would have been injected, and it is objectionable for a person to carry several injectors with him for a long period of time. Therefore, one single device is desired in which more different injection liquids which may not be in contact with each other for a longer period of time can be stored while separated from each other, but with which, if necessary, the injection liquids can be injected simultaneously or substantially simultaneously. Such a device is known from U.S. Pat. No. 3,572,336. Injection liquids which are poorly compatible or are not at all compatible with each other can be injected simultaneously by means of the device described and shown in said Patent Specification. For that purpose, a number of medicament holders are in operative association with a number of needles or with one needle via a mixing chamber. A piston is present in each medicament holder, while the collective pistons are connected through separate piston rods to one common piston rod so that under the influence of a coiled spring the medicament holders can simultaneously be emptied. The injector known from the above-mentioned United States Patent Specification is very complicated and hence less reliable than would be desired. In fact, the possibility of a component not operating satisfactorily, as a result of which the injector would fail at the critical moment, is the larger according as the device comprises more components which are to give the desired result in cooperation with each other. In addition, the cost-price of such a complicated device will be high, as a result of which one may be inclined to replace the device less rapidly than is desirable; as a result of this the reliability of the system is also adversely influenced.

Another "plural injecting device" is known from European Patent Application No. 14006. The device described in said Application consists of a number of separate automatic single-compartment injectors which are together assembled in one outer casing in such manner that upon activation of one of the injectors the other ones also become operative so that all injection liquids are simultaneously injected. This device is destined in particular for military application. The composition of enemy's battle gases varies regularly so that it is desired to replace from time to time in stored automatic injectors an antidote which is active against a given battle gas component. This can be done particularly easily in the "plural injecting device" known from the last-mentioned Patent Application, namely by simply exchanging one of the single-compartment injectors therein by one having a different antidote. However, the disadvantage of the "plural injecting device" described in the above-mentioned Patent Application is the bulkiness and the weight, as a result of which said device is less easy to carry and to use in case of need.

It is the object of the invention to provide an automatic device for injecting two or more different injection liquids which may not be in contact with each other for a longer period of time, which device must satisfy the following conditions: (1) easy handlability, (2) reliability, and (3) simplicity of construction so that the cost of manufacture can be kept low.

This object can be achieved by means of an automatic injector, comprising a combination of a discharge mechanism, a cartridge holder and a cartridge which is slidably accommodated in the cartridge holder and which comprises an ampoule, a piston which is movable in the ampoule and seals same, and a hypodermic needle which is connected to the front of the ampoule by means of a needle mount, and, if desired, is covered by a flexible sheath to maintain the needle in a sterile condition, which device according to the invention is characterized in that the ampoule between the piston and the needle mount comprises one or more stoppers which are movable in the ampoule and which, before use of the device, keep the injection liquids present in the ampoule separated from each other in that their circumference adjoins the inner wall of the ampoule in a sealing manner, and that the needle mount comprises a collar connected to the front of the ampoule in a sealing manner, a neck in which the injection needle is connected, and an entirely or substantially cylindrical shaft between collar and neck, a passage being formed in the inner wall of the shaft and the rear face of the neck past which the injection liquid or injection liquids can reach the cannula when during use of the device the stopper or stoppers is or are moved into the shaft of the needle mount.

A very important additional advantage of the device according to the invention is the flexibility of the liquid compartments. In the known injectors the contents of the liquid compartments are determined by the dimensions of the medicament holders, while the number of liquid compartments is entirely fixed once a given construction has been chosen. On the other hand, the contents of the liquid compartments of the device according to the invention is fully variable because the distance between the piston and the stopper, between the stopper and the needle connection, and, if more stoppers are present, between the stoppers mutually can be adjusted at will. The number of liquid compartments can also be chosen at will by varying the number of stoppers in the ampoule between piston and needle mount; only the length of the by-pass means for the injection liquid or liquids must be adapted to the overall length of the collective stoppers. The by-pass means in the needle mount, between the inner wall of the shaft and the rear face of the neck on the one hand and the stopper or stoppers moved forwards into the shaft on the other hand, as a result of which the injection liquid or liquids can reach the cannula, may be formed, for example, by providing that the inner wall of the shaft of the needle mount has a circular or oval cross-section, that the rear face of the neck of the needle mount comprises a few spacing supports, and that the room bounded by the inner wall of the shaft and the spacing supports on the rear face of the neck has a slightly larger circumference than the expanded stopper or stoppers and is slightly longer than the stopper or the collective stoppers, so that the stopper or the collective stoppers in the extreme forward position can fill this room substantially entirely but in which an aperture remains around the stopper or stoppers.

The spacing supports may be three or four projections, for example in the form of caps or truncated cones.

In another embodiment, instead of the spacing supports on the rear face of the neck of the needle mount the front face of the stopper nearest to the rear face of the neck of the needle mount comprises a few spacing supports, while the room bounded by the inner wall of the shaft and the rear face of the neck of the needle mount has a slightly larger circumference than the expanded stopper or stoppers and is slightly longer than the stopper of the collective stoppers including the spacing supports.

In another preferred embodiment the inner wall of the shaft of the needle mount comprises one or more ridges which extend in the longitudinal direction of the shaft over a length which is slightly larger than the length of the stopper or the collective stoppers, and the front face of the stopper nearest to the rear face of the neck of the needle mount comprises a few spacing supports, so that upon actuation of the device the stopper or stoppers are deformed when contacting the ridge or ridges, so that a by-pass is formed allowing the injection liquid or liquids behind the stopper or stoppers to reach the cannula past the stopper or stoppers.

Alternatively, instead of the spacing supports on the front face of the stopper, the rear face of the neck of the needle mount comprises a few spacing supports. In the latter case the spacing supports preferably form one or more ridges as an extension of the ridge or ridges on the inner wall of the shaft.

As already explained, the number of liquid compartments in the device according to the invention may be varied at will by providing more or fewer stoppers in the ampoule between the piston and the needle mount. When the length of the stoppers is fixed, the device according to the invention in the above-described preferred embodiments may simply be provided with a needle mount with matched shaft length.

Although the ampoule is preferably manufactured from glass, also a rigid form-retaining synthetic material may be used, provided that this material is not permeable for the injection liquids, sufficiently vapour-tight and compatible with the medicaments. The needle mount is manufactured from a form-retaining synthetic material by a moulding process. The foremost injection liquid is preferably present between the foremost stopper and the needle connection, so in the room bounded by the inner wall of the shaft of the needle mount, the rear face of the neck of the needle mount, and the front face of the foremost stopper. Of course the material of the needle mount should be impermeable for the foremost injection liquid, sufficiently vapour-tight and compatible with the medicament in said injection liquid.

BRIEF DESCRIPTION OF THE DRAWINGS

The invention will now be described in greater detail with reference to preferred embodiments which are shown in the drawings, in which.

DESCRIPTION OF THE PREFERRED EMBODIMENTS

Figure 1:
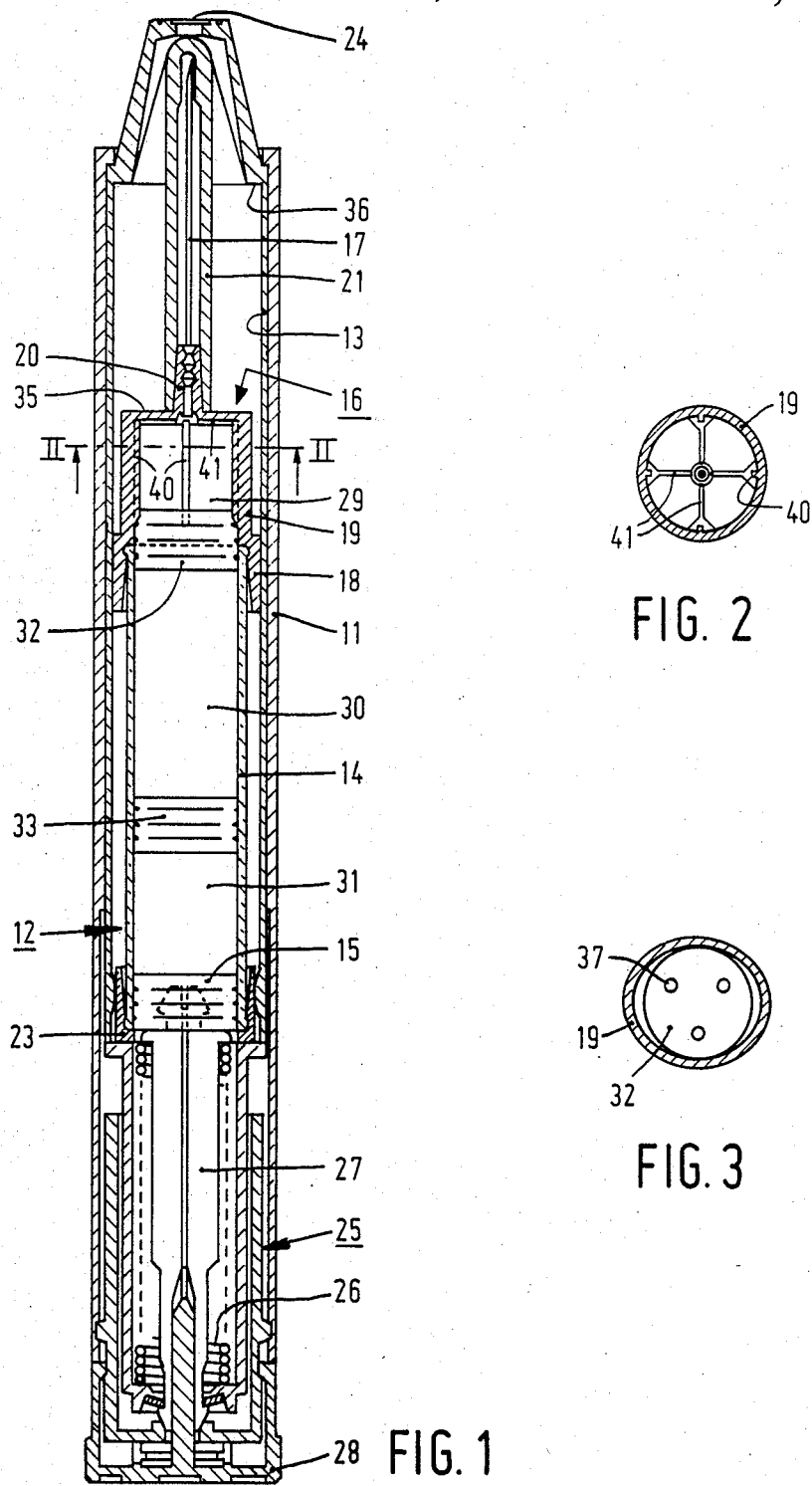
FIG. 1 is a longitudinal sectional view of an injection device according to the invention in the condition in which it can be transported and stored.
Figure 2:
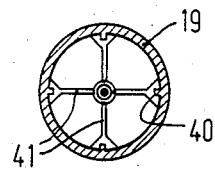
FIG. 2 is a cross-sectional view through the needle mount of the device of FIG. 1, viz. taken on the line II—II of FIG. 1, viewed in the direction of the injection needle.

The injection device shown in FIGS. 1 and 2 is constructed for the greater part as described in detail and shown in Netherlands Patent Specification No. 160.725 in the name of Applicants. In broad outline the device comprises a cylindrical outer sleeve 11 in which a cartridge assembly 12 is provided so as to be slidable, comprising a cartridge holder sleeve or inner sleeve 13 fitting in the outer sleeve, a cylindrical glass ampoule 14 containing injection liquids, a piston 15 at one end and a needle mount 16 with injection needle 17 at the other end of the ampoule. At each end the ampoule comprises a radically outwardly projecting flange around which on the side of the injection needle the needle mount is connected by means of a collar 18. The needle mount furthermore comprises a shaft 19 which is cylindrical for the greater part and a neck 20 in which the needle 17 having a flexible needle guard 21 is connected.

The inner wall of the shaft is provided with four ridges 40, extending in the longitudinal direction and having an approximately rectangular cross-section. The rear face of the neck of the needle mount also comprises four ridges 41 as extensions of and integrally formed with ridges 40. The needle mount is manufactured from a form-retaining synthetic material by moulding.

An externally cylindrical sliding sleeve 23 which is slidable in the cartridge holder sleeve 13 is connected around the flange at the other end of the ampoule. The cartridge assembly 12 is provided in the outer sleeve 11 in such manner that the closed end of the needle guard 21 bears against the end of the cartridge holder sleeve 13 having a bore 24.

The outer sleeve 11 has such a length that the cartridge assembly 12 is accommodated in one end and the discharge mechanism 25 is accommodated in the other end. The discharge mechanism which comprises a coil spring 26 as a power source is exactly equal to the spring power assembly described in the above-mentioned Netherlands Patent Specification No. 160,725, and comprises locking means 27 and a safety device 28.

Internally the ampoule 14 is divided into three separated liquid compartments 29, 30 and 31 by means of two cylindrical stoppers 32 and 33 which, like the piston, have a slightly larger diameter than the inside diameter of the ampoule. These stoppers, as well as the piston, are manufactured from a flexible material, preferably rubber of a pharmaceutical quality. The shaft of the needle mount, apart from the ridges, has an inside diameter which is approximately equal to, but preferably slightly larger than that of the ampoule. Furthermore, the ridges on the shaft are slightly longer than the two stoppers collectively, so that the ends of the ridges remote from the needle connection have just become uncovered when the stoppers have been moved forward entirely to against the ridges on the rear face of the neck of the needle mount. When the injection device shown in FIGS. 1 and 2 is actuated, the cartridge assembly moves forward under the influence of the spring, the sliding sleeve 23 moving in the cartridge holder sleeve. The needle guard is compressed, the needle perforating the closed end of the needle guard and entering into the body in that place where the injection is to be administered. When the needle is in its foremost position, in which the needle mount is stopped in that the front of the part 35 of the needle mount connecting the shaft and the neck abuts against a shoulder 36 formed by a constriction in the cartridge holder neck, the forward movement of the piston begins under the influence of the same spring, so that a beginning of the actual injection is made. The injection liquid in compartment 29 is now injected, the whole assembly of piston 15, stoppers 32 and 33 and liquid columns 30 and 31 moving forward.

The elastic stopper 32 is deformed during passage of the ridges, small ducts being formed on either side of each ridge. When the stopper 32 has moved in the shaft over such a distance that the rear face of said stopper has past the ends of the ridges remote from the needle connection, the injection liquid in compartment 30 can reach the cannula through the small ducts.

When all the injection liquid from the compartments 29 and 30 has been injected, the front face of stopper 32 is present just against the ridges on the rear face of the neck of the needle mount and stoppers 32 and 33 bear against each other. At that instant stopper 33 has moved forward over such a distance that the rear face of said stopper leaves the ends of the ridges remote from the needle connection just uncovered so that the injection liquid in compartment 31 can also reach the cannula and can be injected.

Figure 3:
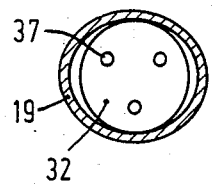
FIG. 3 is a cross-sectional view through the needle mount of a device taken along the same line as shown in FIG. 1, but this time of a different embodiment of the needle mount of the device in accordance with the invention and viewed in the direction of the stopper.

In another embodiment the inner wall of the shaft of the needle mount has a slightly larger circumference than the expanded stoppers so that the injection liquids behind the stoppers can pass the stoppers when these have been moved into the shaft. The shaft of the needle mount may have a circular or oval cross-section; the latter shape is shown in FIG. 3. The rear face of the neck of the needle mount or the front face of the front stopper comprises spacing supports, for example, in the form of caps or truncated cones. The cross-section shown in FIG. 3 is viewed in the direction of the front stopper 32, the front face of the stopper comprising three projections 37.

I claim:

1. An automatic device for injecting two or more different injection liquids which may not be in contact with each other for long periods of time, comprising a combination of a discharge mechanism, a cartridge holder and a cartridge which is slidably accommodated in the holder and which comprises an ampoule, a piston which is movable in the ampoule and seals same, and a hypodermic needle connected to the front of the ampoule by means of a needle mount, and, if desired, covered by a flexible sheath to maintain the needle in a sterile condition, said device being characterized in that said cartridge includes said injection liquids and the ampoule between the piston and the needle mount comprises one or more stoppers which are movable in the ampoule and which, before use of the device, keep the injection liquids present in the ampoule separated from each other in that their circumference adjoins the inner wall of the ampoule in a sealing manner, and that the needle mount comprises a collar connected to the front of the ampoule in a sealing manner, a neck in which the injection needle is connected, and an entirely or substantially cylindrical shaft between the collar and the neck, a passage being formed in the inner wall of the shaft and the rear face of the neck past which the injection liquid or injection liquids can reach the needle when during use of the device the stopper or stoppers is or are moved into the shaft of the needle mount; the inner wall of the shaft of the needle mount having a circular or oval cross-section, the rear face of the neck of the needle mount comprising a plurality of spacing supports; and the region bounded by the inner wall of the shaft and the spacing supports on the rear face of the neck having a slightly larger circumference than the expanded stopper or stoppers and being slightly longer than the stopper or the collective stoppers, so that the stopper or the collective stoppers in the extreme forward position can fill this region substantially entirely but in which an aperture remains around the stopper or stoppers; and said collar including means for maintaining the ampoule in radially spaced relationship from said holder.

2. An automatic device for injecting two or more different injection liquids which may not be in contact with each other for long periods of time, comprising a combination of a discharge mechanism, a cartridge holder and a cartridge which is slidably accommodated in the holder and which comprises an ampoule, a piston which is movable in the ampoule and seals same, and a hypodermic needle connected to the front of the ampoule by means of a needle mount, and, if desired, covered by a flexible sheath to maintain the needle in a sterile condition, said device being characterized in that said cartridge includes said injection liquids and the ampoule between the piston and the needle mount comprises one or more stoppers which are movable in the ampoule and which, before use of the device, keep the injection liquids present in the ampoule separated from each other in that their circumference adjoins the inner wall of the ampoule in a sealing manner, and that the needle mount comprises a collar connected to the front of the ampoule in a sealing manner, a neck in which the injection needle is connected, and an entirely or substantially cylindrical shaft between the collar and the neck, a passage being formed in the inner wall of the shaft and the rear face of the neck past which the injection liquid or injection liquids can reach the needle when during use of the device the stopper or stoppers is or are moved into the shaft of the needle mount; the inner wall of the shaft of the needle mount having a circular or oval cross-section, the front face of the stopper nearest to the rear face of the neck of the needle mount comprising a plurality of spacing supports, and the region bounded by the inner wall of the shaft and the rear face of the neck of the needle mount having a slightly larger circumference than the expanded stopper or stoppers and being slightly longer than the stopper or the collective stoppers including the spacing supports, so that the stopper or the collective stoppers in the extreme forward position can fill this region substantially entirely but in which an aperture remains around the stopper or stoppers; and said collar including means for maintaining the ampoule in radially spaced relationship from said holder.

3. An automatic device for injecting two or more different injection liquids which may not be in contact with each other for long periods of time, comprising a combination of a discharge mechanism, a cartridge holder and a cartridge which is slidably accommodated in the holder and which comprises an ampoule, a piston which is movable in the ampoule and seals same, and a hypodermic needle connected to the front of the ampoule by means of a needle mount, and, if desired, covered by a flexible sheath to maintain the needle in a sterile condition, said device being characterized in that said cartridge includes said injection liquids and the ampoule between the piston and the needle mount comprises one or more stoppers which are movable in the ampoule and which, before use of the device, keep the injection liquids present in the ampoule separated from each other in that their circumference adjoins the inner wall of the ampoule in a sealing manner, and that the needle mount comprises a collar connected to the front of the ampoule in a sealing manner, a neck in which the injection needle is connected, and an entirely or substantially cylindrical shaft between the collar and the neck, a passage being formed in the inner wall of the shaft and the rear face of the neck past which the injection liquid or injection liquids can reach the needle when during use of the device the stopper or stoppers is or are moved into the shaft of the needle mount; the inner wall of the shaft of the needle mount comprising one or more ridges which extend in the longitudinal direction of the shaft over a length which is slightly larger than the length of the stopper or the collective stoppers, the front face of the stopper nearest to the rear face of the neck of the needle mount comprising a plurality of spacing supports, so that upon actuation of the device the stopper or stoppers are deformed when contacting the ridge or ridges, so that a by-pass is formed allowing the liquid or liquids behind the stopper or stoppers to reach the needle past the stopper or stoppers; and said collar including means for maintaining the ampoule in radially spaced relationship from said holder.

4. An automatic device for injecting two or more different injection liquids which may not be in contact with each other for long periods of time, comprising a combination of a discharge mechanism, a cartridge holder and a cartridge which is slidably accommodated in the holder and which comprises an ampoule, a piston which is movable in the ampoule and seals same, and a hypodermic needle connected to the front of the ampoule by means of a needle mount, and, if desired, covered by a flexible sheath to maintain the needle in a sterile condition, said device being characterized in that said cartridge includes said injection liquids and the ampoule between the piston and the needle mount comprises one or more stoppers which are movable in the ampoule and which, before use of the device, keep the injection liquids present in the ampoule separated from each other in that their circumference adjoins the inner wall of the ampoule in a sealing manner, and that the needle mount comprises a collar connected to the front of the ampoule in a sealing manner, a neck in which the injection needle is connected, and an entirely or substantially cylindrical shaft between the collar and the neck, a passage being formed in the inner wall of the shaft and the rear face of the neck past which the injection liquid or injection liquids can reach the needle when during use of the device the stopper or stoppers is or are moved into the shaft of the needle mount; the inner wall of the shaft of the needle mount comprising one or more ridges which extend in the longitudinal direction of the shaft over a length which is slightly larger than the length of the stopper or the collective stoppers, the rear face of the neck of the needle mount comprising a plurality of spacing supports, so that upon actuation of the device the stopper or stoppers are deformed when contacting the ridge or ridges, so that a by-pass is formed allowing the injection liquid or liquids behind the stopper or stoppers to reach the needle past the stopper or stoppers; and said collar including means for maintaining the ampoule in radially spaced relationship from said holder.

5. A device as claimed in claim 4, characterized in that the spacing supports on the rear face of the neck of the needle mount form one or more ridges as an extension of the ridge or ridges on the inner wall of the shaft.

6. A device as claimed in claim 1, wherein the inner surface of said holder is substantially cylindrical over substantially the entire length traveled by said cartridge upon actuation of said device.

7. A device as claimed in claim 2, wherein the inner surface of said holder is substantially cylindrical over substantially the entire length traveled by said cartridge upon actuation of said device.

8. A device as claimed in claim 3, wherein the inner surface of said holder is substantially cylindrical over substantially the entire length traveled by said cartridge upon actuation of said device.

9. A device as claimed in claim 4, wherein the inner surface of said holder is substantially cylindrical over substantially the entire length traveled by said cartridge upon actuation of said device.

10. A device as claimed in claim 5, wherein the inner surface of said holder is substantially cylindrical over substantially the entire length traveled by said cartridge upon actuation of said device.

* * * * *